ns Patent [19]

Schultz et al.

[11] Patent Number: 5,037,640

[45] Date of Patent: Aug. 6, 1991

[54] SKIN COLORING AND SUNSCREENING COMPOSITIONS CONTAINING INDOLES AND M-NITRO ALKOXYBENZENES

[75] Inventors: Thomas M. Schultz, Highland Mills, N.Y.; George Serban, Ridgefield, Conn.; Alexander C. Chan, Mineola, N.Y.

[73] Assignee: Clairol Incorporated, New York City, N.Y.

[21] Appl. No.: 440,571

[22] Filed: Nov. 22, 1989

[51] Int. Cl.$^5$ .................. A61K 7/021; A61K 7/40; A61K 7/42; A61K 9/10

[52] U.S. Cl. ........................... 424/59; 424/47; 424/63; 514/781; 514/847; 514/937; 514/938; 514/939; 514/944; 514/969

[58] Field of Search .................... 424/59, 63

[56] References Cited

U.S. PATENT DOCUMENTS

| 3,491,114 | 1/1970 | Suh | 424/59 X |
|---|---|---|---|
| 3,501,465 | 3/1970 | Shen et al. | 424/59 X |
| 4,776,857 | 10/1988 | Carroll et al. | 424/63 |
| 4,832,943 | 5/1989 | Grollier et al. | 424/63 |

Primary Examiner—Dale E. Ore
Attorney, Agent, or Firm—S. Nolan

[57] ABSTRACT

Compositions containing selected indoles and m-nitro alkoxybenzenes are useful for imparting a tan coloration to the skin while concurrently functioning as sun screening compositions.

10 Claims, 4 Drawing Sheets

X   mixture of 5,6-methylenedioxyindole and m-nitroanisole
Δ   5,6-methylenedioxyindole
O   m-nitroanisole Time of Irradiation (minutes)

X mixture of 5,6-methylenedioxyindole and 3-propoxynitrobenzene
O 5,6-methylenedioxyindole X mixture of 5,6-methylenedioxyindole and 3-propoxynitrobenzene
O 5,6-methylenedioxyindole

SKIN COLORING AND SUNSCREENING COMPOSITIONS CONTAINING INDOLES AND M-NITRO ALKOXYBENZENES

FIELD OF THE INVENTION

This invention is concerned with cosmetic compositions containing selected indoles and m-nitro alkoxybenzenes which are useful to impart coloration to the skin and to afford protection against harmful rays of the sun.

BACKGROUND OF THE INVENTION

Skin, tanning is generally perceived to enhance personal appearance. The skin plays an important role in our social interaction. Since it is our outer covering, skin provides the first visual impression of our individuality. Its appearance often generates judgements on sensual appeal, beauty and even health. A suntan has integrated itself into the appearance aesthetics of skin with the result that suntanned skin is regarded not only as desirable and attractive but also possesses the attribute of health. As a result, many individuals actively seek a tan by exposing themselves to the sun. Such exposure, as is well known from human experience, often results in painful erythema or sun burn. It may also result in premature aging of the skin, certain types of dermatological diseases and even skin cancer.

The art has, therefore, long sought chemical agents which will impart to the skin the characteristic bronze color of a natural tan, but will do so without extensive and potentially dangerous exposure or with minimum exposure to the sun. Such agents must be easily available, inexpensive, non-toxic, stable on storage and capable of imparting an even, long lasting natural-looking coloration to the human skin.

One of the first agents found to be effective in generating a tan coloration to the human skin was dihydroxyacetone. Unfortunately, this material was found to be more reactive with some areas of the skin than others resulting in a speckled appearance, and, in some cases, an unpleasant yellowish color.

Tanning is believed to be the result of melanin formation, a reaction which is triggered by the action of sunlight, principally the UV component of sunlight.

The actual mechanism by which melanin forms in the human body is not a part of this invention. It believed that melanin is a polymer containing several indole segments formed as a result of the cyclization and subsequent polymerization of dihydroxyphenylalanine (DOPA) caused by exposure to the sun.

Not surprisingly, the art has turned to indoles as of possible utility in coloring the skin. As a result, it has been observed that many indoles will cause the topically formed melanin to give a tanned appearance to the skin. European Patent Publication 0,239,896 is representative of one such effort. That patent describes the coloration of skin by the use of such indoles.

Coloration by indoles is believed to occur by photolytic oxidation under the influence of sunlight or some other source of ultraviolet light. The reaction is very slow and it may take very large doses of energy to convert the indoles to a detectable tan. As a result the skin remains unprotected and erythema develops.

On the earth's surface, sunlight spectrum ranges from 290 nm to 1,850 nm in wavelength. Infrared light, which has the lowest energy in the sunlight spectrum, covers from 1,850 nm to ca. 750 nm. Visible light ranges from ca. 750 nm to 400 nm. Sunlight with even higher energy is known as ultraviolet light, and it is further divided into UVA (400 nm–320 nm) and UVB (320 nm–290 nm). It is believed that UVB exposure is principally responsible for the symptoms of sunburn or other skin diseases. However, it is now thought that UVB and UVA combined are more deleterious than either one alone. Therefore, recent efforts in the sunscreen industry are focused on formulating sunscreens capable of blocking both regions of the ultraviolet spectrum.

THE DRAWING

FIGS. 1–4 are graphs showing certain of the results observed in the examples of this specification.

DETAILED DESCRIPTION OF THE INVENTION

It has now been discovered that the formation of melanin to color the skin by the action of an indole in the presence of sunlight can be accelerated by concurrent use of m-nitro alkoxybenzene, and that color formation can be effected without erythema. For convenience, the m-nitro alkoxybenzene will be hereinafter sometimes referred to as m-nitroanisole since this is the most preferred member of the class.

The indole/m-nitroanisole combinations of the invention will impart a deep, long lasting tan which will form on the skin to which it is applied after exposure to sunlight, but without harmfully affecting the skin.

The invention therefore comprises skin coloring compositions which protect against harmful ultraviolet rays containing a sufficient amount of an indole/m-nitro alkoxybenzene to be tinctorially effective for the formation of the characteristic bronze appearance of a tan.

A particularly advantage of the present invention is that the mixture can protect the skin from both UVA and UVB irradiation from the sun since the indoles absorb largely in the UVB region and the nitroanisoles can absorb both UVA and UVB light. Upon irradiation by sunlight, the nitroanisoles absorb most of the solar energy which is then transferred to the indoles, causing them to polymerize and form a tan colored product in the skin. This new combination, consequently, protects the skin from the harmful sunlight while at the same time imparting a tan colored appearance to the skin. Since the tan colored product forms in the skin it is not washable from the skin. In addition the newly formed colored product provides further protection from the sunlight.

The indoles and m-nitro alkoxybenzenes presently preferred for use in this invention are represented by the following formulas A, B and C:

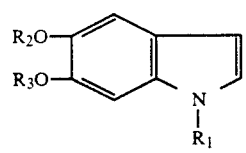

A

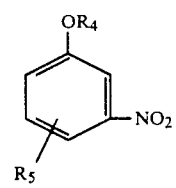

B

-continued

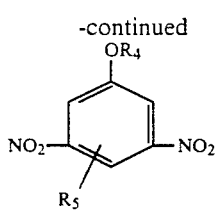

C wherein:

$R_1$ is hydrogen, $C_1$–$C_6$ alkyl, $C_1$–$C_6$ hydroxyalkyl, or alkoxyalkyl containing a total of 2 to 6 carbon atoms;

$R_2$ and $R_3$ which may be the same or different are hydrogen, $C_1$–$C_{12}$ alkyl or $C_1$–$C_{18}$ acyl; or $R_2$ and $R_3$ may together form a ring; $R_4$ is $C_1$–$C_{23}$ alkyl and $R_5$ is H or $C_1$–$C_{18}$ alkyl.

Each composition of this invention will contain at least one compound represented by formula A together with a compound represented by formulas B, C or mixtures thereof.

At present, the most preferred compounds of this invention are those in which the various R groups contain up to three carbon atoms.

The most preferred indoles are those in which the nitrogen atom is substituted with a hydrogen or a methyl group and the substituents at the 5- and 6- positions are hydroxyl, methoxyl, acetoxy or methylene dioxy. More specifically these compounds are:
5,6-methylenedioxyindole,
N-methyl-5,6-methylenedioxyindole, 5,6-dimethoxyindole,
N-methyl-5,6-diacetoxyindole, and
N-methyl-5,6-dihydroxyindole.

These compounds together with m-nitroanisole are preferred because they are available without excessive difficulty and because they are particularly effective in achieving the objectives of the invention.

A particular advantage of the composition of this invention compared to indoles alone is that the color produced in accordance with it is closer to a natural tan. As is well known to those skilled in the art, the use of indoles in low concentration on the skin produces a greyish tint. At high concentrations the color tends to be closer to black.

The compositions of this invention are preferably aqueous compositions. The term aqueous composition is used herein in its usual generic sense as embracing any water-containing composition useful for the present purposes. This includes true solutions of the selected compounds in an aqueous medium either alone or in conjunction with other materials, which are also dissolved or dispersed in the aqueous medium. The term aqueous composition also encompasses any mixture of the compounds used in the invention in the aqueous medium either alone or together with other ingredients. The various components may be colloidally dispersed in the medium or may merely be intimately mixed therein. Moreover, the aqueous medium may comprise water or water and an additional or auxiliary solvent. Typical auxiliary solvents which may be used to enhance the solubility of the components include ethanol, carbitol, isopropanol, propylene glycol, ethylene glycol, diethylene glycol, diethylene glycol monoethyl ether, glycerine, etc.

The aqueous compositions of this invention can be prepared by conventional methods used in the art. Thus, they can be prepared by dissolving or suspending the components in the selected media with adequate mixing. Preparation may take place at ambient temperatures, i.e., 20° to 35°, but solubility and rate of preparation can be enhanced utilizing elevated temperatures, for example 40° to 100° C.

Well known conventional additives usually employed in cosmetic compositions of this type such as thickeners, surface active agents, antioxidants, fragrances and chelating agents may be included in the compositions of the inventions. Such compositions are preferably liquid solutions but they may be in the form of emulsions, suspensions, lotions, or gels.

Surface active agents employed in the compositions of the invention can be anionic, nonionic or cationic. By way of examples of the various types of surface active agents, there can be mentioned: higher alkylbenzene sulfonates; alkylnaphthalenesulfonates; sulfonated esters of alcohols and polybasic acids; taurates; fatty alcohol sulfates; sulfates of branched chain or secondary alcohols; alkyldimethylbenzylammonium chlorides, salts of fatty acids or fatty acid mixtures; N-oxyalkylated fatty acid alkanolamides, and the like. Illustrative of specific surfactants there can be mentioned; sodium lauryl sulfate; polyoxyethylene lauryl ester; myristyl sulfate; glyceryl monostearate; triethanolamine oleate, sodium salt of palmitic methyl taurine; cetyl pyridnium chloride; lauryl sulfonate; myristyl sulfonate; lauric diethanolamide; polyoxyethylene stearate; ethoxylated oleoyl diethanolamide; polyethylene glycol amides of hydrogenated tallow; stearyldimethyl benzyl ammonium chloride; dodecylbenzene sodium sulfonate; 2-amino-2-methyl propanol; triethanolamine salt of p-dodecylbenzene sulfonate; triethanolamine salt of p-dodecylbenzene sulfonate; nonylnaphthalene sodium sulfonate; dioctyl sodium sulfosuccinate; sodium N-methyl-N-oleoyl taurate; oleic acid ester of sodium isothionate; sodium dodecyl sulfate; the sodium salt of 3-0-diethyl tridecanol-6-sulfate and the like. The quantity of surface active agent can vary over a wide range, such as from about 0.05% to 15% and preferably from about 0.10 to 5% by weight of the composition. Mixtures of different surfactants and different types of surfactants are also included within the scope of the invention.

A thickening agent may also be incorporated in the compositions. These includes, for example, such products as sodium alginate or gum arabic, or cellulose derivatives, such as methylcellulose, e.g., Methocel 60HG, or the sodium salt of carboxymethylcellulose, or hydroxyethylcellulose, e.g., Cellosize QP-40 or acrylic polymers, such as polyacrylic acid sodium salt, or inorganic thickeners, such as bentonite. The quantity of the selected thickening agent can also vary over a wide range, even as high as 20%. Ordinarily it will range from about 0.5 to 5% by weight of the composition. The viscosity of the composition may vary from about 1 cps to about 100,000 cps. For a typical lotion formulation, composition viscosity is between about 100 cps to about 10,000 cps.

It may also be useful to incorporate one or more antioxidants. A variety of antioxidants are known in the art which are useful for this purpose. Among these, mention may be made of the inorganic sulfites, e.g., sodium sulfite; thioglycollic acid and other mercaptans; butylated hydroxytoluene; sodium dithionite; various forms of ascorbic acid and its derivatives, e.g., sodium ascorbate, erthorbic acid, ascorbyl palmitate, ascorbyl laurate, etc. The quantity of anitoxidant when in use can vary appreciably. However, this will, in general, be up to about 1%, typically 0.001 to 1% by weight.

The concentration of the selected indole and nitroanisole in the compositions of this invention may vary over a wide range depending principally on the intensity of the color change desired. Other factors readily evaluated by those skilled in the art will also be taken into consideration. These include the degree of sun protection desired, and the rate of color development.

Typically, the amount of indole or mixture of indoles in the cosmetic compositions will be from about 0.1% to 10% based on the total weight of the composition. On the same basis, the amount of m-nitro alkoxybenzenes, or mixtures thereof is normally from about 0.1% to 10%. The preferred amounts are 0.5 to 2.0% indole and 0.5 to 6% m-nitro alkoxybenzene. Typically, the ratio of indole to m-nitro alkoxybenzene will be from 1:0.05 to 1:10, preferably 1:0.5 to 1:1.5.

The compositions of the invention may be packaged using conventional techniques appropriate to the composition type e.g., liquid solutions or suspensions, gels, creams, ointments, etc. Liquid compositions are especially suitable for aerosol packaging in which the composition is packaged under pressure with a propellant such as a compressed gas or a liquified hydrocarbon or halogenated hydrocarbon such as butane or trichlorofluoromethane. The composition exits the container under pressure through a metering valve which may be especially designed to spread the skin coloring composition evenly over the skin surface to be treated.

In the method of the invention, the desired tanning is imparted to the skin by topical application of the selected composition by manually spreading on the area where the tan is desired, by spraying or other equivalent means.

The following examples are given by way of illustration only and should not be considered as limitations of the invention.

In the examples, color formation (tan) was measured using the Hunter Tristimulus Colorimeter. With this instrument, light/dark is represented as "L" value (decreasing value is darker) and the shade or hue by the "a" and "b" values. These values are arbitrarily selected so that +a is red, −a is green, +b is yellow and −b is blue. Thus, a gray or black color will have "a" and "b" values close to zero. A typical tan color will have strongly positive "a" and "b" values representing the reddish and yellowish brown color of a desirable tan shade.

FIG. 1 is a graph showing changes in L values, ΔL (i.e., degree of darkness of the tan color) on excised skin as a function of the irradiation time. The skin was treated with 5,6-methylenedioxyindole (Δ), m-nitroanisole (O), or a mixture of the two (X).

FIG. 2 is a graph showing changes in L values (ΔL) on pig skin as a function of the irradiation time. Two independent experimental results are included. The skin was treated with a mixture of 5,6-methylenedioxyindole and 3,5-dinitroanisole.

EXAMPLE 1

Color formation from indole derivatives in the presence of m-nitroanisole is exemplified by the following in-vitro experiments. Table I lists the four indoles tested. The indole ($3 \times 10^{-4}$M) and m-nitroanisole ($9 \times 10^{-4}$M) were dissolved in 25% isopropyl alcohol/water. The solutions where photolysed for 5 min. in a Rayonet mini-photochemical reactor equipped with four low pressure mercury lamps, which have maximum emission between 330-380 nm. After this time the absorption spectra of the solution was run between 420 and 600 nm. Increased absorption in this region reflects product (tan color) formation. Areas under the products absorption curves were integrated—the larger integrated area representing more product formation. Results are given in Table 1. Indole solutions containing the anisole developed color upon photolysis, but solutions without the catalyst (i.e., the controls) give no colored product. In the case of 5,6-dihydroxy-N-methylindole, some color was observed in the control solution, since this compound is unstable in aqueous solution and undergoes oxidation by air to give color. However, it is clear that the anisole does have a significant effect on the rate of pigment formation in solution. This example also demonstrates the potential efficiency of the catalyst in protecting the skin against UV-A irradiation. It absorbs long wavelength ultraviolet light and utilizes this energy to induce pigment formation from the indoles.

| INDOLE | | INTEGRATED AREA (Arbitrary unit) | COLOR |
|---|---|---|---|
| 5,6-methylenedioxy-N-methylindole | catalysed | 990 | reddish brown |
|  | control | 0 | colorless |
| 5,6-dimethoxyindole | catalysed | 2000 | reddish brown |
|  | control | 0 | colorless |

| INDOLE | | INTEGRATED AREA (Arbitrary unit) | COLOR |
|---|---|---|---|
| 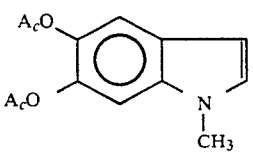 | catalysed control | 220 0 | yellowish brown colorless |
| 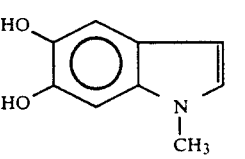 | catalysed control | 2720 590 | brown light brown |

TABLE I

Effect of m-Nitroanisole on the Colored Product Formation from Indoles.

| INDOLE | INTEGRATED AREA (Arbitrary unit) | COLOR |
|---|---|---|
| catalysed | 990 | reddish brown |
| control | 0 | colorless |
| catalysed | 2000 | reddish brown |
| control | 0 | colorless |
| catalysed | 220 | yellowish brown |
| control | 0 | colorless |
| catalysed | 2720 | brown |
| control | 590 | light brown |

The remaining examples show that the effects that are observed in solution, can also be observed on live or excised skin.

EXAMPLE 2

Figure 1:
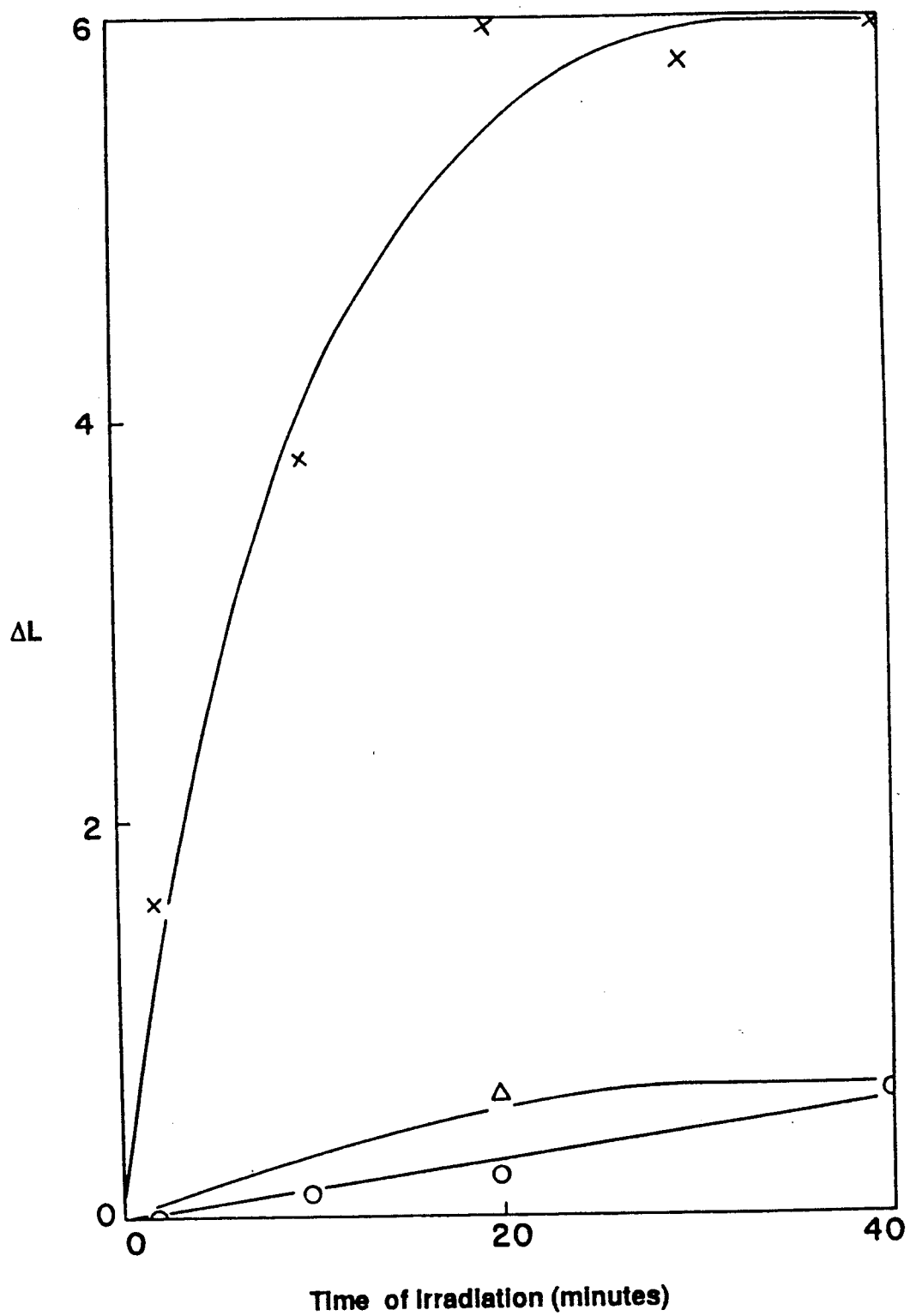

A mixture of m-nitroanisole (3%) and 5,6-methylenedioxyindole (1%) in 70% isopropyl alcohol/water was applied to excised skin for 30 min. The treated area could be optionally washed with soap and water before being irradiated with a solar simulator at minimum erythema dose. A tan color developed on the skin readily and was not removable by washing with water. The change in intensity of the color (represented by ΔL, where L is one of the parameters in Hunter tristimulus values to indicate the degree of darkness of a color) on skin versus the length of UV-irradiation is plotted in FIG. 1(curve a). The rapid increase in the intensity is obvious. However, very little color was produced when either m-nitroanisole or 5,6-methlenedioxyindole alone is applied and irradiated over the same period of time (curve b and c). In addition, the skin was colored a pleasing golden brown by the mixture (Hunter Tristimulus values L 60.1, a 8.6, b 16.4).

The Hunter "a" and "b" values reflects the shade of the color (+a is red, −a is green, +b is yellow, −b is blue). A black or gray color has a and b values close to zero. Thus in this case the high positive a and b values reflect the brown tan color.

EXAMPLE 3

Figure 2:
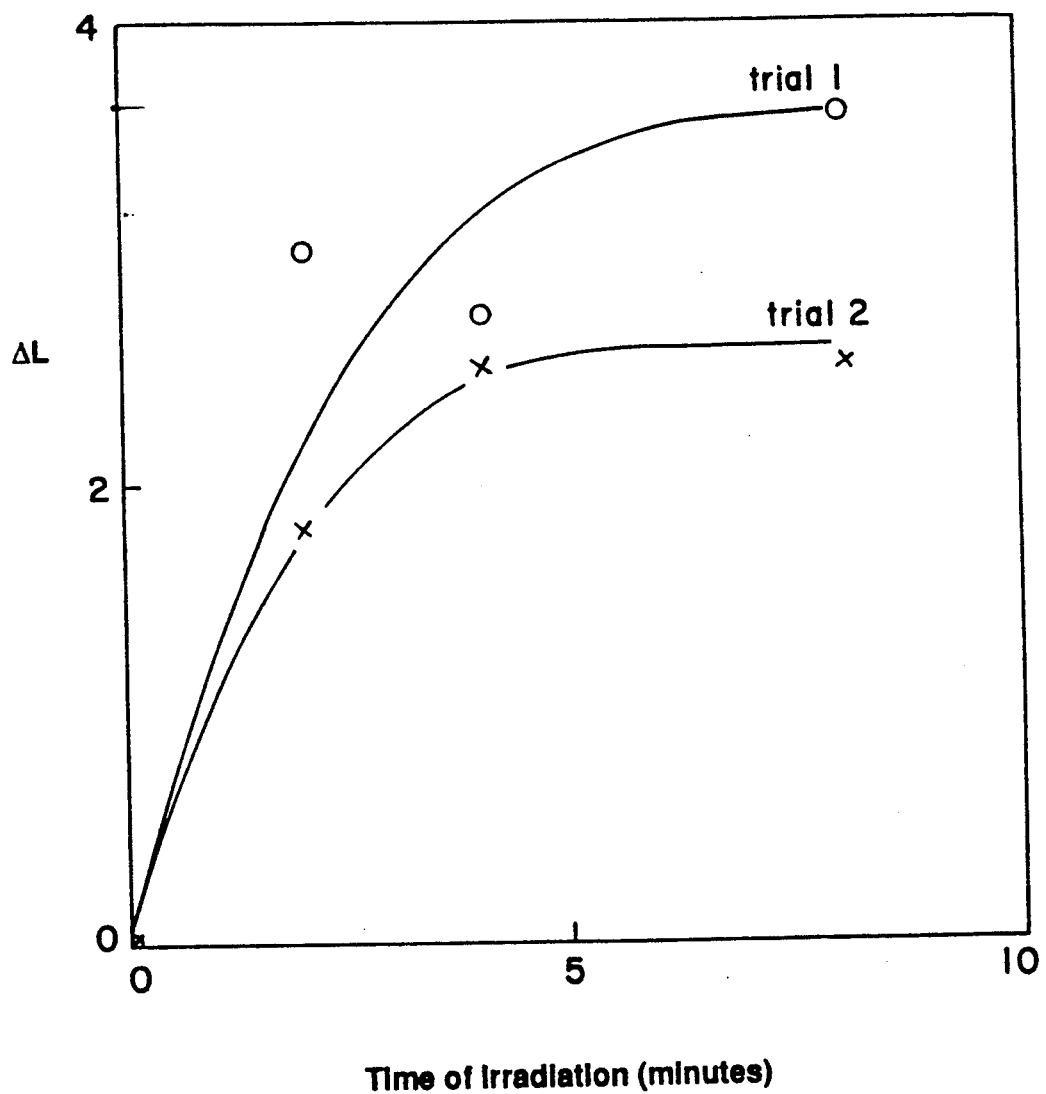

A solution of 5,6-methylenedioxyindole (1%) and 3,5-dinitroanisole (2%) in acetone/isopropyl alcohol/water (50:30:20) was applied to the flanks of hairless guinea pigs. After 30 min., the treated sites were thoroughly washed with soap and then irradiated with a solar simulator using doses corresponding to those needed to produce minimum erythema in the average caucasian human skin. A pleasing tan color developed. FIG. 2 shows two independent trials, and similar results were obtained. On the other hand, very little color was observed on the site treated with the indole solution alone. After additional exposure to UV irradiation, the indole/anisole composition treated site darkens further, but the sites treated with the indole alone only redden. This is an indication of erythema (skin reddening). In contrast the skin treated with the mixture was reddish brown (Hunter Tristimulus values L 62.2, a 7.6, b 8.5).

EXAMPLE 4

A solution (water-isopropanol-acetone 1:2:1.2), 5,6-methylenedioxyindole (0.1%) and 3-propoxynitrobenzene (0.7%) was applied to skin of live guinea pig for 30 minutes. The treated area was irradiated with a 150 watt Xenon short arc lamp. Immediately after irradiation, the tristimulus L values were taken (see Example 2 for definition) and the rate of blood flow near the skin surface were also measured. It is known that the rate of blood flow near the surface of the skin is proportional to the degree of erythema. Hence a lower rate represents better skin protection by the mixture.

Figure 3:
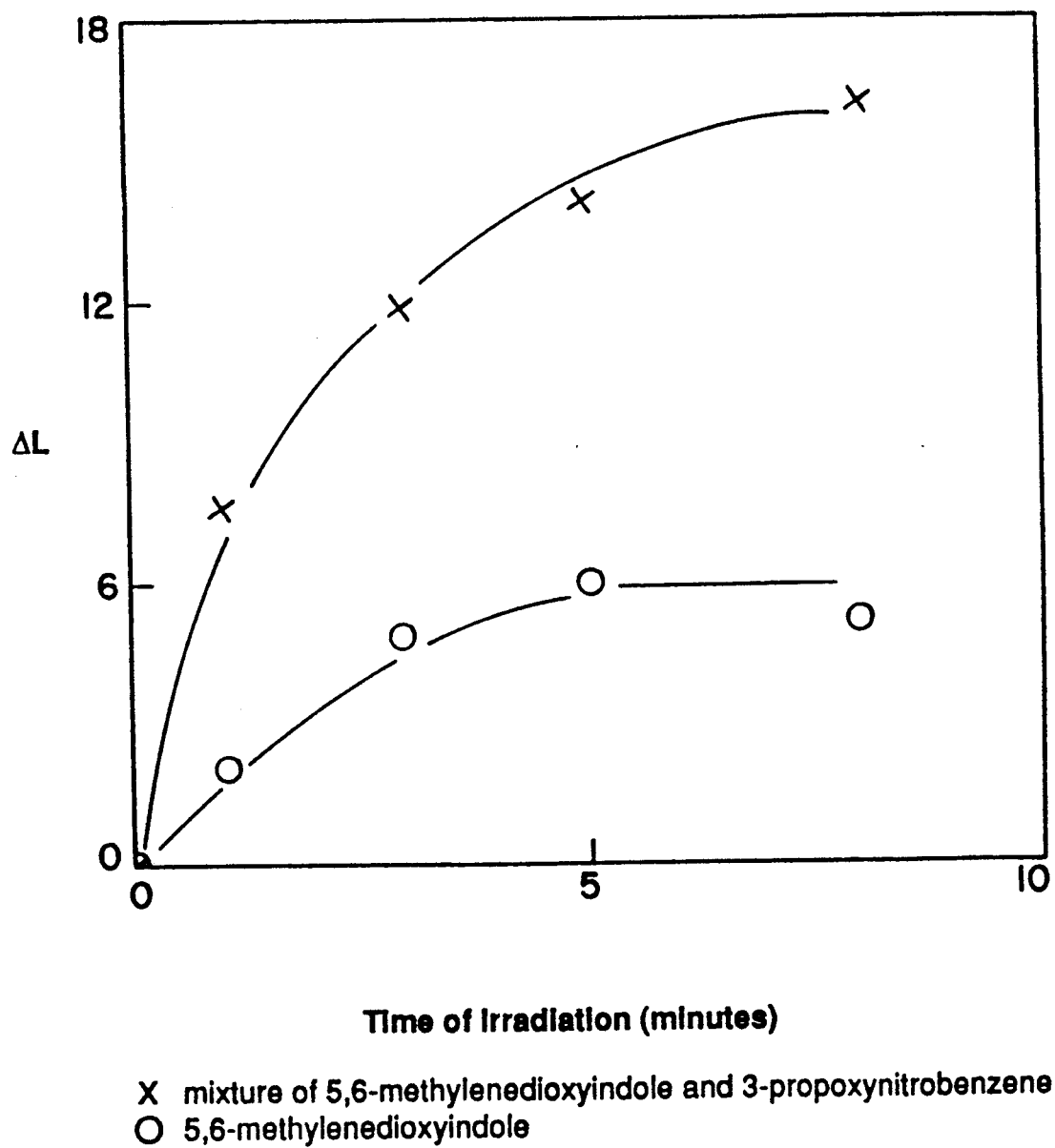
FIG. 3 is a graph showing changes in L values (ΔL) on guinea pig skin as a function of irradiation dosage. In the figure, X represents change in color intensity on the skin surface due to the mixture of Example 4, and O represents change in color intensity on the skin treated with 5,6-methylenedioxyindole.
Figure 4:
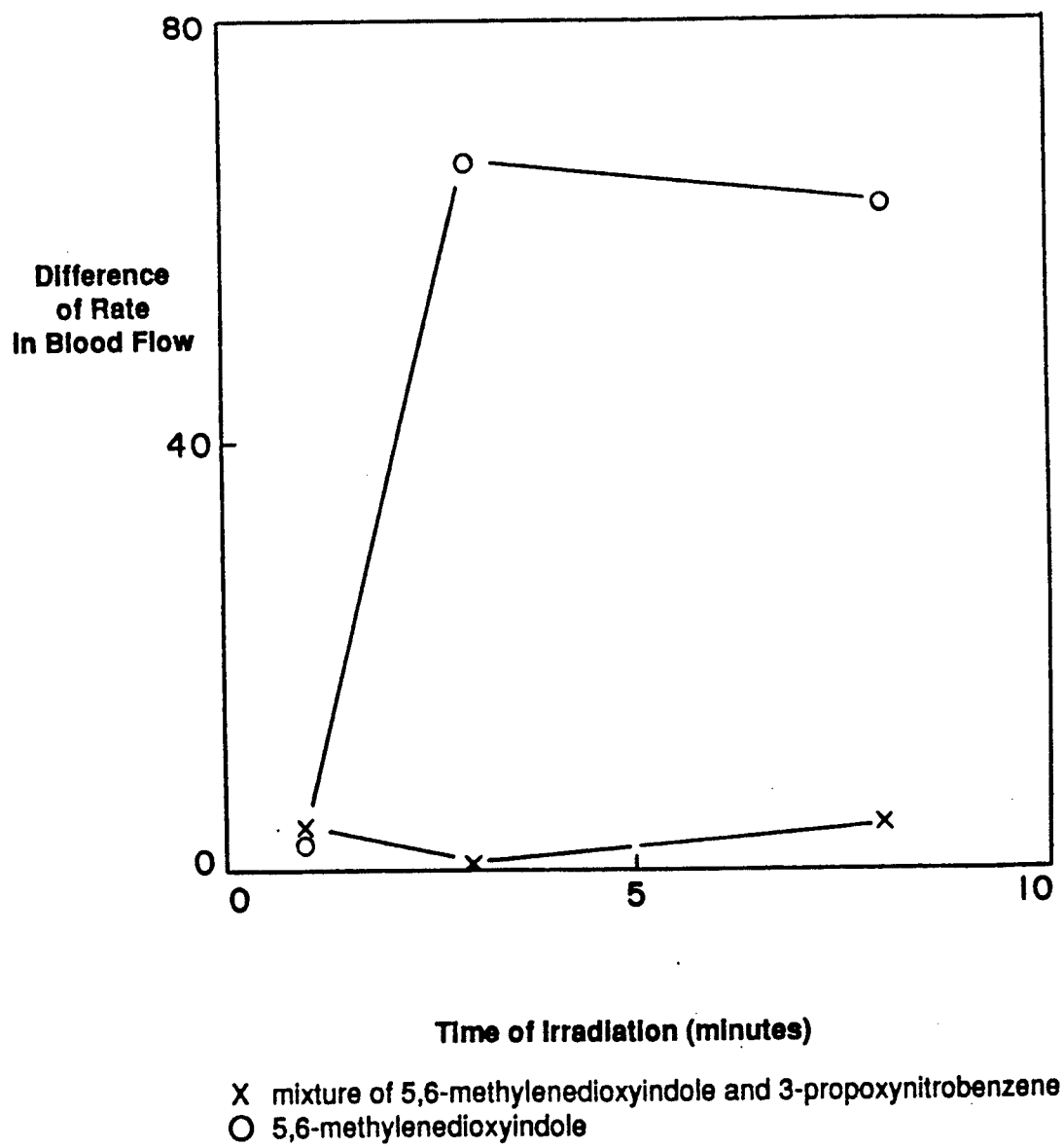
FIG. 4 is a graph showing changes in rate of blood flow on the skin surface as a function of irradiation dosage. In the figure, X represents difference of rate in blood flow on the skin surface treated with the mixture of Example 4, and O represents the difference of rate in blood flow on the untreated skin surface.

The results are given in FIG. 3 which clearly demonstrates the higher efficiency of color product formation compared with the use of indole alone. Furthermore, the rate of blood flow is fairly constant and only increases significantly on the irradiated spot which was not treated with the solution (FIG. 4). Hence the sunscreening effect of this mixture is also apparent.

After the treatment the skin was colored a pleasant golden tan (L 53.6, a 7.2, b 15.2).

What is claimed is:

1. A cosmetic composition for imparting a tanned appearance to the skin while concurrently protecting it from the the harmful ultraviolet rays comprising a cosmetically acceptable carrier together with a tinctorially effective amount for tanning the skin of a mixture of compounds represented by the following formulas A, B or C:

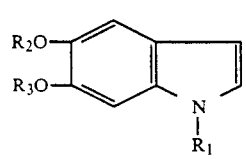

A

-continued

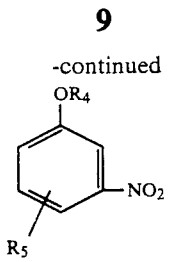
B

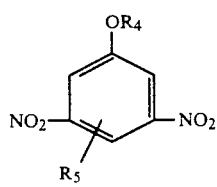
C wherein $R_1$ is hydrogen, $C_1$-$C_6$ alkyl, $C_1$-$C_6$ hydroxyalkyl, or alkoxyalkyl containing a total of 2 to 6 carbon atoms;

$R_2$ and $R_3$ which may be the same or different are hydrogen, $C_1$-$C_{12}$ alkyl or $C_1$-$C_{18}$ acyl; or $R_2$ and $R_3$ may together form a ring; $R_4$ is $C_1$-$C_{23}$ alkyl; and $R_5$ is H or $C_1$-$C_{18}$ alkyl, there being at least one compound represented by formula A and a compound represented by formula B or C or mixtures thereof in each composition.

2. A composition of claim 1 containing, based on the total weight of the composition, from 0.1% to 10% of a compound of formula A and from 0.1% to 10% of a compound of formula B.

3. A composition of claim 1 wherein the compound of formula A is 5,6-diacetoxy-N-methyl indole and the compound of formula B is m-nitroanisole.

4. A composition of claim 2 wherein the compound of formula A is 5,6-diacetoxy-N-methyl indole and the compound of formula B is m-nitroanisole.

5. A composition of claim 1 wherein the compound of formula A is 5,6-diacetoxyindole and the compound of formula B is m-nitroanisole.

6. A composition of claim 2 wherein the compound of formula A is 5,6-diacetoxyindole and the compound of formula B is m-nitroanisole.

7. A process for coloring skin while concurrently protecting it from the harmful rays of the sun comprising topically engaging to the skin the composition of claim 1.

8. A process for coloring skin while concurrently protecting it from the harmful rays of the sun comprising topically applying to the skin the composition of claim 2.

9. A process for coloring skin while concurrently protecting it from the harmful rays of the sun comprising topical application to the skin of a composition of claim 3.

10. A process for coloring skin while concurrently protecting it from the harmful rays of the sun comprising topical application to the skin of a composition of claim 5.

* * * * *